US00PP31819P3

(12) United States Plant Patent
Pan

(10) Patent No.: US PP31,819 P3
(45) Date of Patent: May 26, 2020

(54) ***HELIANTHUS* PLANT NAMED 'SUR67-1'**

(50) Latin Name: ***Helianthus* x *interspecific***
Varietal Denomination: SUR67-1

(71) Applicant: SYNGENTA CROP PROTECTION AG, Basel (CH)

(72) Inventor: Shifeng Pan, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,037

(22) Filed: Feb. 12, 2019

(65) Prior Publication Data

US 2019/0254217 P1 Aug. 15, 2019

Related U.S. Application Data

(60) Provisional application No. 62/629,813, filed on Feb. 13, 2018.

(51) Int. Cl.
*A01H 5/02* (2018.01)
*A01H 6/14* (2018.01)

(52) U.S. Cl.
USPC ..... Plt./436
CPC ..... *A01H 6/1464* (2018.05)

(58) Field of Classification Search
USPC ..... Plt./436
CPC ..... A01H 5/02; A01H 6/14
See application file for complete search history.

*Primary Examiner* — Annette H Para
(74) *Attorney, Agent, or Firm* — Dale Skalla

(57) ABSTRACT

A new *Helianthus* plant named 'SUR67-1' particularly distinguished by the medium to large size yellow decorative inflorescences, vigorous size plant, round mound plant habit, with a natural flowering response of early May until late September.

1 Drawing Sheet

Latin name of the genus and species of the plant claimed: *Helianthus* x *interspecific*.

Varietal denomination: 'SUR67-1'.

BACKGROUND OF THE NEW PLANT

The present invention comprises a new *Helianthus*, botanically known as *Helianthus* x *interspecific* hybrid, and hereinafter referred to by the variety name 'SUR67-1'.

'SUR67-1' is a product of a planned breeding program. The new cultivar has medium to large size yellow decorative type inflorescences, medium large size plant, mound spreading plant habit, with a natural flowering response of early June and last to early September in garden.

'SUR67-1' originated from a hybridization made in July 2011 in a greenhouse in Gilroy, Calif. The female parent was a commercially available *Helianthus Interspecific* Hybrid Yellow Dark Center 70052828 (SUO22=SUL1) (U.S. patent application Ser. No. 15/747,160) with similar flower color, larger flower size, less number of flowers. This female parent has high bush type plants and similar earliness on flowering time in garden than that of 'SUR67-1'.

The unpatented male parent of 'HELAB0103-2V' was selected from a population grown from *Helianthus debilis* species, a commercially available packet seed, with small yellow flower and having a distinctly small leaf, and very well branched mound bush plant. The resultant seed was sown in March 2011 and the young plants HELAB0103-2V was selected in June 2011 in greenhouse in Gilroy, Calif. USA.

'SUR67-1' was selected as one flowering plant within the progeny of the stated cross in late June 2012 in Gilroy, Calif.

The first act of asexual reproduction of 'SUR67-1' was accomplished when vegetative cuttings were propagated from the initial selection in a greenhouse in Gilroy, Calif. in December 2012.

BRIEF SUMMARY OF INVENTION

Horticultural examination of plants grown from cuttings of the plant initiated in December 2012, and continuing thereafter, has demonstrated that the combination of characteristics as herein disclosed for 'SUR67-1' are firmly fixed and are retained through successive generations of asexual reproduction.

'SUR67-1' has not been observed under all possible environmental conditions. The phenotype may vary slightly with variations in environment such as temperature, light intensity, and day length.

'SUR67-1' has not been made publicly available more than one year prior to the filing of this application.

The following traits have been repeatedly observed and are determined to be basic characteristics of the new variety. The combination of these characteristics distinguishes this *Helianthus* as a new and distinct variety.

BRIEF DESCRIPTION OF THE PHOTOGRAPHS

The accompanying photographic drawings show typical flower and foliage characteristics of 'SUR67-1' with colors being as true as possible with an illustration of this type.

Figure 1:
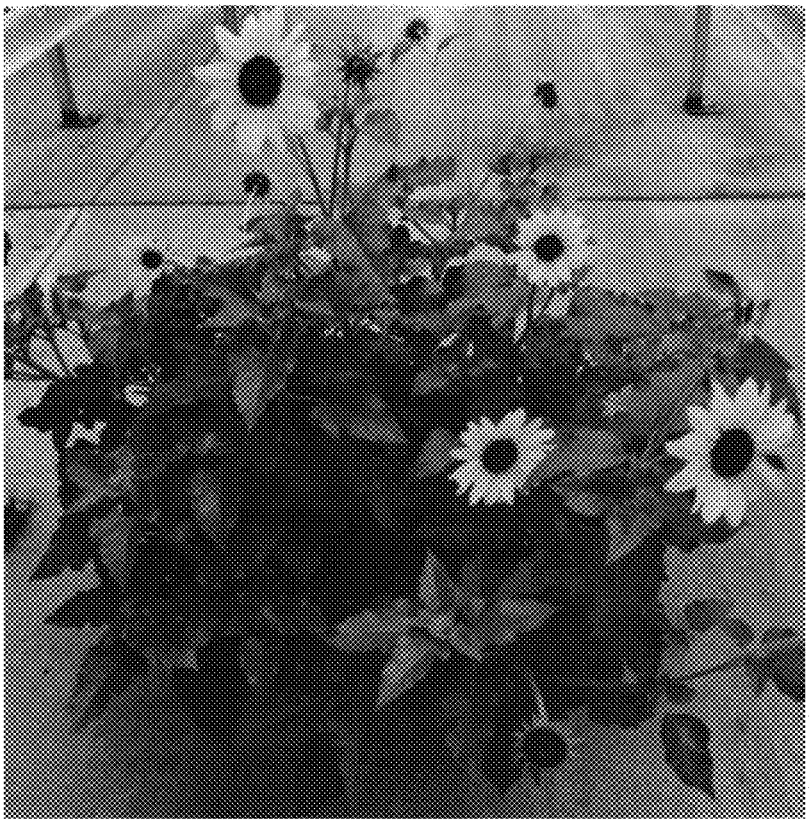
Figure 2:
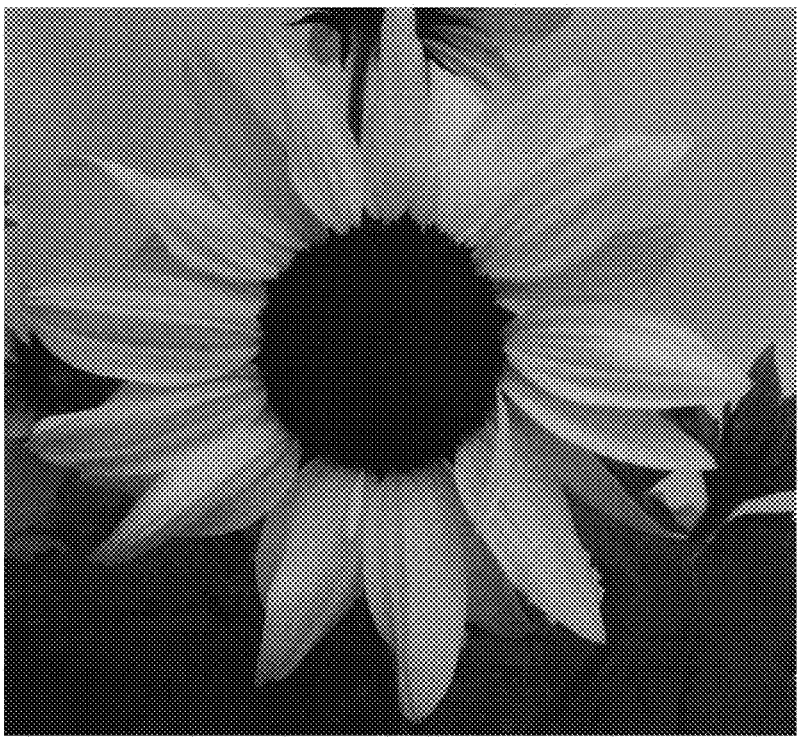

FIG. 1 shows a flowering potted plant of the new variety and FIG. 2 shows a close-up of the flowers.

DETAILED BOTANICAL DESCRIPTION

The plant descriptions and measurements were taken in Gilroy, Calif. in late April 2018 outdoors in natural light.

These plants were grown in gallon pots in a greenhouse trial and were about 14 weeks old. These plants were pinched at 3rd internode early growing stage.

The aforementioned photographs were taken in April 2018 in Gilroy, Calif. These plants were about 14 weeks of age. They were grown one plant per gallon pot. These plants were pinched.

Color references are made to The Royal Horticultural Society Colour Chart (R.H.S.) 2001.

TABLE 1

DIFFERENCES BETWEEN THE NEW VARIETY 'SUR67-1' AND MOST SIMILAR VARIETIES

| | 'SUR67-1' | 'SUO22=SUL1' (U.S. patent application 15/747,160) |
|---|---|---|
| Flower type and color: | Same | Similar |
| Plant habit: | Rounder, wider, and less upright | More upright |
| Plant strength: | Strong | Stronger |
| Flower color: | Dark yellow | Yellow |
| Plant size: | Large | Medium-large |

Plant:

*Form, growth and habit.*—Herbaceous garden-type, stems upright and outwardly spreading, freely branching, strong and moderately vigorous growth habit.

*Plant height.*—14-16 cm.

*Plant height (inflorescence included).*—20-22 cm.

*Plant width.*—42-45 cm.

Roots:

*Number of days to initiate roots.*—About 4-6 days at about 22 degrees C.

*Number of days to produce a rooted cutting.*—14-16 days at 22 degrees C.

*Type.*—Thick, strong, massive.

*Color.*—RHS N155B but whiter.

Foliage:

*Arrangement.*—Alternate.

*Immature, leaf color, upper surface.*—RHS 147A.

*Immature, leaf color, lower surface.*—RHS 146A.

*Mature, leaf color, upper surface.*—RHS 147A.

*Mature, leaf color, lower surface.*—RHS 146A.

*Length.*—4.5-5.2 cm.

*Width.*—2.9-3.3 cm.

*Shape.*—Ovate.

*Base shape.*—Attenuate.

*Apex shape.*—Rounded to obtuse.

*Margin.*—3 main lobes, and irregularly serrulate.

*Texture, upper surface.*—Bifid hair.

*Texture, lower surface.*—Bifid hair.

*Color of veins, upper surface.*—RHS 144B.

*Color of veins, lower surface.*—RHS 144B.

*Pattern of veining.*—Palmate.

*Petiole color.*—RHS 144B.

*Length.*—0.9-1.1 cm.

*Diameter.*—0.15-0.2 cm.

*Texture.*—Bifid hair.

Stem:

*Quantity of main branches per plant.*—15-20.

*Color of stem.*—From RHS 137A to RHS 137B.

*Length of stem.*—About 20-25 cm.

*Diameter.*—0.25-0.30 cm.

*Length of internodes.*—1.00-2.50 cm.

*Texture.*—Covered with bifid hair.

*Color of peduncle.*—RHS 138B.

*Length of peduncle.*—5.5-7.1 cm.

*Peduncle diameter.*—0.15 cm.

*Texture.*—Covered with bifid hair.

Inflorescence:

*Type.*—Compositae, solitary, decorative-type inflorescences borne terminally above foliage, ray florets arranged on a capitulum.

*Quantity of short days to flowering (response time).*—6.5 weeks.

*Natural season flowering.*—Early September.

*Quantity of inflorescences per plant.*—55-60, plus many additional buds in various stages of development.

*Lastingness of individual blooms on the plant.*—About 6 weeks from the first color depending on conditions.

*Fragrance.*—Slightly spicy.

Bud (just when opening/showing color):

*Color.*—RHS 7A.

*Length.*—2.0-2.7 cm.

*Width.*—2.0-2.5 cm.

*Shape.*—Oblate.

Immature inflorescence:

*Diameter.*—5.5-5.8 cm.

*Color of ray florets, upper surface.*—RHS 7A.

*Color of ray florets, lower surface.*—RHS 7B.

Mature inflorescence:

*Diameter.*—6.0-6.6 cm.

*Depth.*—2.0-2.5 cm.

*Total diameter of disc.*—Small, covered by the many rays.

*Receptacle color.*—RHS 145B.

*Receptacle height.*—0.4 cm.

*Receptacle diameter.*—0.25 cm.

Ray florets:

*Average quantity of florets.*—About 8-10.

*Color of florets, upper surface.*—RHS 6A.

*Color of florets, lower surface.*—RHS 6A.

*Length.*—Approximately 3.5-5.0 cm.

*Width.*—0.5-0.75 cm.

*Shape.*—Oblong to elliptical.

*Apex shape.*—Most often emarginate or praemorse.

*Base shape.*—Cuneate.

*Margin.*—Entire.

*Texture, upper surface.*—Papillate.

*Texture, lower surface.*—Papillate.

*Texture, lower surface.*—Bifid hairs.

Disc florets:

*Average quantity of florets.*—30-55.

*Color of florets.*—RHS 1B, or slightly more greenish.

*Length.*—0.2-0.35 cm.

*Width.*—0.1 cm.

*Shape.*—Tubular, elongated.

*Apex shape.*—Acute, 5 pointed.

Reproductive organs:

*Pistil.*—1, found on both types of florets.

*Length.*—0.5-0.6 cm.

*Style color.*—RHS 1C.

*Style length.*—0.35-0.40 cm.

*Stigma color.*—RHS 7D.

*Stigma shape.*—Bi-lobed.

*Ovary color.*—RHS 145C.

*Ovary length.*—0.15 cm.

*Ovary width.*—0.1 cm.

*Stamens.*—4, found on only on the disc florets.
*Color of filaments.*—RHS 155C.
*Length filaments.*—0.15 cm.
*Anther color.*—RHS 6A.
*Anther length.*—0.1 cm.
*Anther shape.*—Oblong.
*Color of pollen.*—RHS 15C.
*Pollen amount.*—None.
*Disease/pest resistance.*—Has strong powdery mildew resistance.

What is claimed is:

1. A new and distinct variety of *Helianthus* plant named 'SUR67-1' substantially as illustrated and described herein.

* * * * *